United States Patent
Cable

(10) Patent No.: US 12,102,522 B2
(45) Date of Patent: Oct. 1, 2024

(54) ENDOVASCULAR STENT GRAFT

(71) Applicant: OSF Healthcare System, Peoria, IL (US)

(72) Inventor: David George Cable, Rockford, IL (US)

(73) Assignee: OSF HEALTHCARE SYSTEM, Peoria, IL (US)

( * ) Notice: Subject to any disclaimer, the term of this patent is extended or adjusted under 35 U.S.C. 154(b) by 634 days.

(21) Appl. No.: 17/421,930

(22) PCT Filed: Jan. 9, 2020

(86) PCT No.: PCT/US2020/012919
§ 371 (c)(1),
(2) Date: Jul. 9, 2021

(87) PCT Pub. No.: WO2020/146621
PCT Pub. Date: Jul. 16, 2020

(65) Prior Publication Data
US 2022/0023028 A1     Jan. 27, 2022

Related U.S. Application Data

(60) Provisional application No. 62/790,292, filed on Jan. 9, 2019.

(51) Int. Cl.
*A61F 2/07* (2013.01)
*A61F 2/95* (2013.01)

(52) U.S. Cl.
CPC .......... *A61F 2/07* (2013.01); *A61F 2002/077* (2013.01); *A61F 2002/9511* (2013.01);
(Continued)

(58) Field of Classification Search
CPC .......... A61F 2/07–2002/077; A61F 2250/0003
See application file for complete search history.

(56) References Cited

U.S. PATENT DOCUMENTS

| 5,593,417 A | 1/1997 | Rhodes |
| 2002/0052640 A1 | 5/2002 | Bigus et al. |

(Continued)

FOREIGN PATENT DOCUMENTS

| WO | 2016203040 A1 | 12/2016 |
| WO | 2020146621 A1 | 7/2020 |

OTHER PUBLICATIONS

International Search Report and Written Opinion for PCT/US20/12919 dated Apr. 1, 2020.

(Continued)

*Primary Examiner* — Rebecca S Preston
(74) *Attorney, Agent, or Firm* — Troutman Pepper Hamilton Sanders LLP

(57) ABSTRACT

A stent for endovascular repair in a subject having an aortic dissection or aneurysm in the ascending aorta and methods of using the same are described herein. The stent comprises an inner covered stent having an inner lumen and one or more fenestrations, and an expandable outer shell coupled to the inner covered stent to form a fluid-tight chamber surrounding the inner covered stent. The one or more fenestrations provide fluid communication between the inner lumen and the fluid-tight chamber. The method of using the stent comprises deploying the endovascular stent in a constricted configuration in which the inner covered stent has a reduced diameter. The method further comprises expanding the outer shell to conform to the shape of the ascending aorta and cover an intimal tear of the aortic dissection, and moving the inner covered stent from the constricted configuration to an expanded configuration having an enlarged diameter.

18 Claims, 12 Drawing Sheets

(52) U.S. Cl.
CPC ............ *A61F 2210/0014* (2013.01); *A61F 2220/0008* (2013.01); *A61F 2250/0003* (2013.01); *A61F 2250/0069* (2013.01)

(56) References Cited

U.S. PATENT DOCUMENTS

| | | |
|---|---|---|
| 2004/0098096 A1 | 5/2004 | Eton |
| 2009/0099648 A1 | 4/2009 | Yu |
| 2009/0264993 A1 | 10/2009 | Greenan |
| 2018/0071078 A1* | 3/2018 | Majolagbe ............ A61F 2/07 |
| 2018/0185132 A1* | 7/2018 | Baxter ............ A61F 2/07 |
| 2018/0193131 A1 | 7/2018 | Schreck et al. |

OTHER PUBLICATIONS

European Search Report from European Application No. 22187345.8 dated Nov. 3, 2022.

* cited by examiner

Healthy Aorta
(single lumen)

Transverse View
(layers of aorta)

Dissection
(tear in intima results
in two lumens)

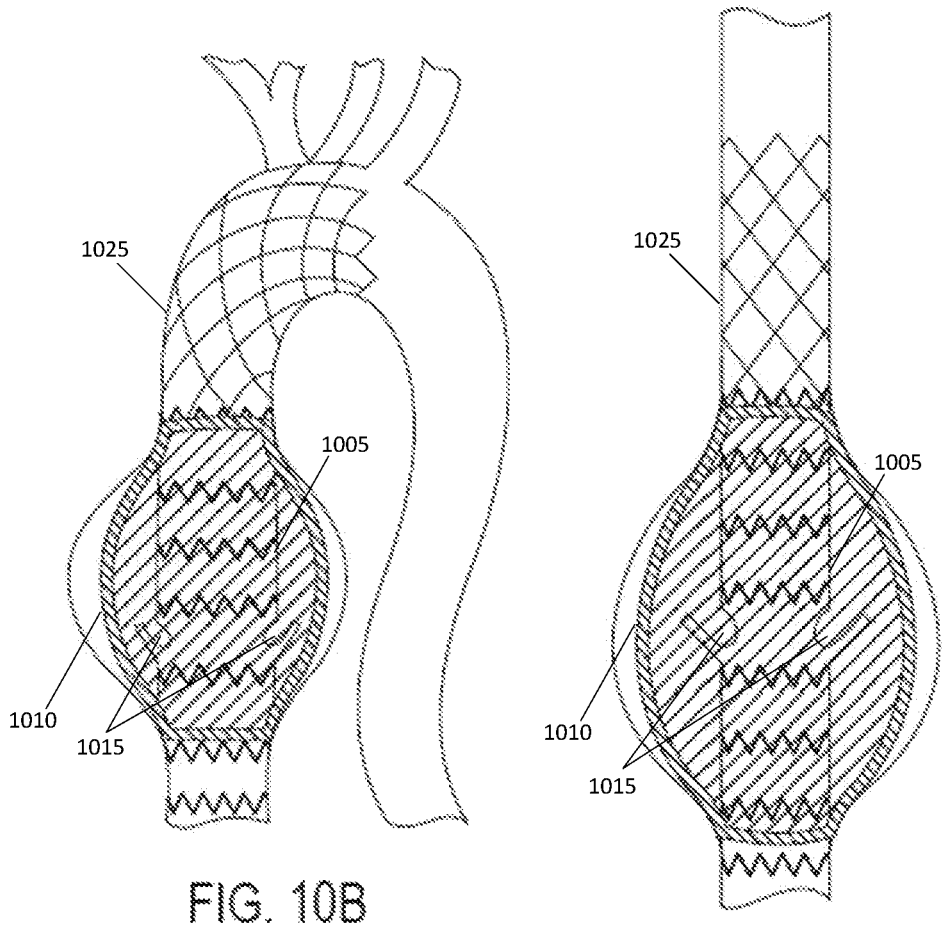
FIG. 10B
FIG. 10C
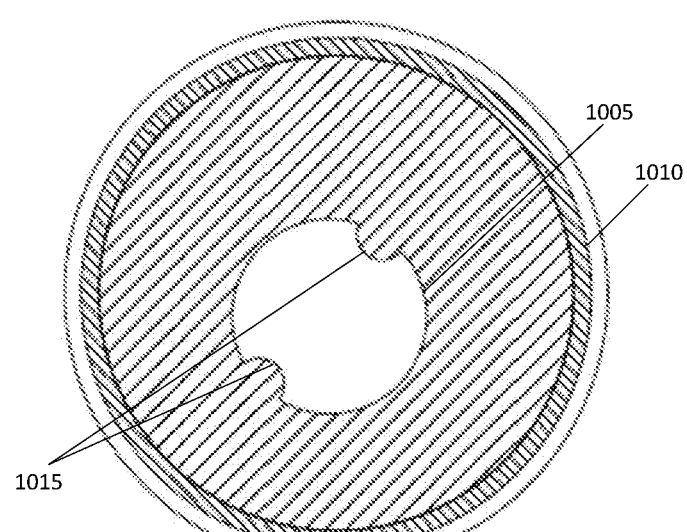
FIG. 10D

ENDOVASCULAR STENT GRAFT

CLAIM OF PRIORITY

This application is a U.S. national stage filing under 35 U.S.C. § 371 of International PCT Application No. PCT/US2020/012919, filed Jan. 9, 2020, which claims the benefit of priority to U.S. Provisional Application No. 62/790,292 entitled "Endovascular Stent Graft," filed Jan. 9, 2019, each of which is incorporated herein by reference in its entirety.

BACKGROUND

Ascending thoracic aortic (TAA) dissections may begin as a tear within the intima of the aorta. This may allow blood to leak into a space between the layers of the aorta creating a "false lumen" that is separate from the normal "true lumen." Ascending thoracic aortic dissections can be a life threatening condition with treatment requiring emergency heart surgery, hypothermic circulatory arrest, and/or blood transfusions.

The aorta comprises three layers: the intima, the media, and the adventitia. Of these layers, the intimal layer is predominately in contact with blood. Further, a tear in the intimal layer is identified as a "fenestration," which provides a connection between the true lumen and a false lumen.

There are various endovascular stent grafts currently on the market for the treatment of descending thoracic and abdominal aortic aneurysms. In addition, some experimental stents have been developed that have not received FDA approval to date. A common design feature of these stent grafts is that the endovascular stent graft is inserted within the blood vessels. Some stent grafts have a covered stent design that allows for blood flow through the stent graft thus excluding the aneurysm from the circulation. This is in contrast to the traditional open surgical procedure in which the aneurysm is resected and replaced with an artificial graft.

Most endovascular stent grafts are placed near a portion of a blood vessel proximal to the aneurysm, also referred to as a proximal landing zone, and a portion of blood vessel distal to the aneurysm, also referred to as a distal landing zone. Such placement allows the stent graft to form a seal with the blood vessel wall. In this manner, the aneurysm is excluded from the circulating blood flow. However, if a seal does not properly develop, the circulating blood flow can enter the aneurysm, which may cause an increased risk of rupturing the aneurysm.

To date, no stent grafts have been developed for the ascending aorta. The ascending aorta is the portion of the blood vessel that exits the heart. The ascending aorta is shorter in length than the descending thoracic or abdominal aorta. As such, the proximal and distal landing zones are shorter in the ascending aorta. Further, the ascending aorta is typically not a straight tube, but rather has an anatomical curvature as it converts to the aortic arch. As such, there are multiple curves within the ascending aorta. The ascending aorta may have a curve from right to left, a curve from anterior to posterior, or a combination thereof. In addition, the ascending aorta curvature may vary from patient to patient. Because of these anatomical differences within and between patients, current commercially available endovascular stent grafts are only suitable for about 40% of patients in need of ascending aorta repair.

A vessel injury in the ascending aorta can result in a life threatening condition called aortic dissection. A dissection of the ascending aorta can cause death in over 95% of patients within the first 24 hours of dissection or rupture if left untreated. Currently, the only treatment option is open surgical intervention that is invasive and requires surgical replacement of the ascending aorta.

What is needed is an endovascular stent graft capable of treating a substantially increased number or all patients in need of ascending aorta repair.

SUMMARY

A method of stabilizing an aortic dissection comprising an intimal tear in an aorta is provided. The method comprises providing an endovascular stent comprising an inner stent having a lumen and one or more fenestrations configured to allow passage of blood; and an expandable outer shell having a first end and a second end and forming a liquid-tight seal to the inner stent at the first end and the second end; and deploying the endovascular stent into the ascending aorta in a constricted configuration, wherein the expandable outer shell is configured to expand responsive to the passage of blood through the one or more fenestrations and apply an outwardly biasing force to the ascending aorta.

According to certain embodiments, the expandable outer shell is further configured to seal the intimal tear.

According to certain embodiments, the expandable outer shell is further configured to compress the aortic dissection.

According to certain embodiments, in the constricted configuration, at least a portion of the inner stent has a reduced diameter. According to additional embodiments, the constricted configuration causes an elevated pressure in the inner lumen, thereby directing blood through the one or more fenestrations. According to additional embodiments, the endovascular stent further comprises a releasable wire constraint configured to maintain the reduced diameter of the inner stent. According to still additional embodiments, the method further comprises releasing the wire constraint to move the inner stent from the constricted configuration to an expanded configuration having an enlarged diameter.

According to certain embodiments, the inner stent comprises a liquid-tight lining between the first end and the second end of the expandable outer shell to form a liquid-tight chamber. According to additional embodiments, each of the one or more fenestrations comprises a one-way valve configured to permit passage of blood from the lumen to the liquid-tight chamber.

According to certain embodiments, the method further comprises anchoring the endovascular stent with a distal anchor to maintain a position of the stent within the ascending aorta. According to additional embodiments, the distal anchor comprises an open, uncovered portion of the inner stent located distally of the second end of the expandable outer shell.

A stent for endovascular repair is also provided. The stent comprises an inner stent having a lumen and one or more fenestrations configured to allow passage of blood; and an expandable outer shell having a first end and a second end and forming a liquid-tight seal to the inner stent at the first end and the second end, wherein the expandable outer shell is configured to expand responsive to the passage of blood through the one or more fenestrations.

According to certain embodiments, the inner stent comprises a liquid-tight lining between the first end and the second end of the expandable outer shell to form a liquid-tight chamber. According to additional embodiments, each of the one or more fenestrations comprises a one-way valve configured to permit passage of blood from the lumen to the liquid-tight chamber.

According to certain embodiments, the inner stent is configurable between a constricted configuration having a reduced diameter and an expanded configuration having an enlarged diameter. According to additional embodiments, the constricted configuration causes an elevated pressure in the inner lumen, thereby directing blood through the one or more fenestrations. According to additional embodiments, the stent further comprises a releasable wire constraint configured to maintain the inner stent in the constricted configuration.

According to certain embodiments, the stent further comprises a distal anchor configured to maintain a position of the stent within a blood vessel. According to additional embodiments, the distal anchor comprises an open, uncovered portion of the inner stent located distally of the second end of the expandable outer shell.

According to certain embodiments, the inner stent is formed from a material selected from the group consisting of nitinol, stainless steel, a shape memory material, a heat activated material, and a combination thereof.

According to certain embodiments, the expandable outer shell is formed from a material selected from the group consisting of polytetrafluoroethylene, polyester, polyethylene terephthalate, polydimethylsiloxane, polyurethane, and a combination thereof.

BRIEF DESCRIPTION OF THE DRAWINGS

FIGS. 10B-10C depict an illustrative endovascular stent implanted in an aorta in accordance with an embodiment.

FIG. 10D depicts a cross-sectional view of an endovascular stent within a blood vessel of a patient in accordance with an embodiment.

DETAILED DESCRIPTION

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The term "patient" and "subject" are interchangeable and may be taken to mean any living organism. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

Some embodiments described herein are directed to systems, methods and apparatuses for treating dissections, aneurysms, or other vasculature injuries. However, it will be appreciated that the systems, methods and apparatuses disclosed herein can be used in other fields or other portions of the body. Some embodiments described herein are directed to systems, methods, and apparatuses to treat lesions, aneurysms, or other defects in the aorta, including, but not limited to, the thoracic, ascending, and abdominal aorta. However, the systems, methods, and apparatuses may have application to other vessels or areas of the body, or to other fields, and such additional applications are intended to form a part of this disclosure. For example, it will be appreciated that the systems, methods, and apparatuses may have application to the treatment of blood vessels in animals. Further, while specific embodiments may be described herein with regard to particular portions of the aorta, it is to be understood that the embodiments described are adaptable for use in other portions of the aorta or other portions of the body and are not limited to the aortic portions described.

Figure 1:
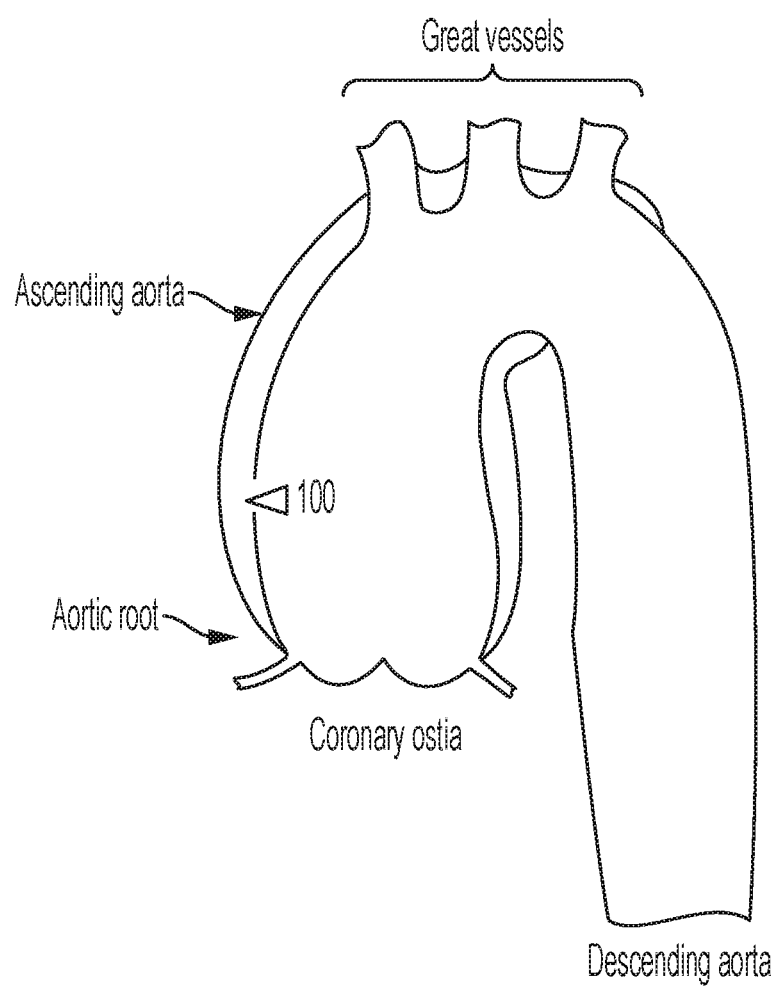
FIG. 1 depicts an illustration of an aorta.

FIG. 1 depicts the anatomy of an aorta including the ascending aorta. Aortic dissection of the ascending aorta may include a tear 100 in the inner lining of the aorta that allows blood to enter the wall of the aorta. A false lumen and/or weakening of the aortic wall may result, either of which can be life threatening without immediate surgery.

Figure 2:
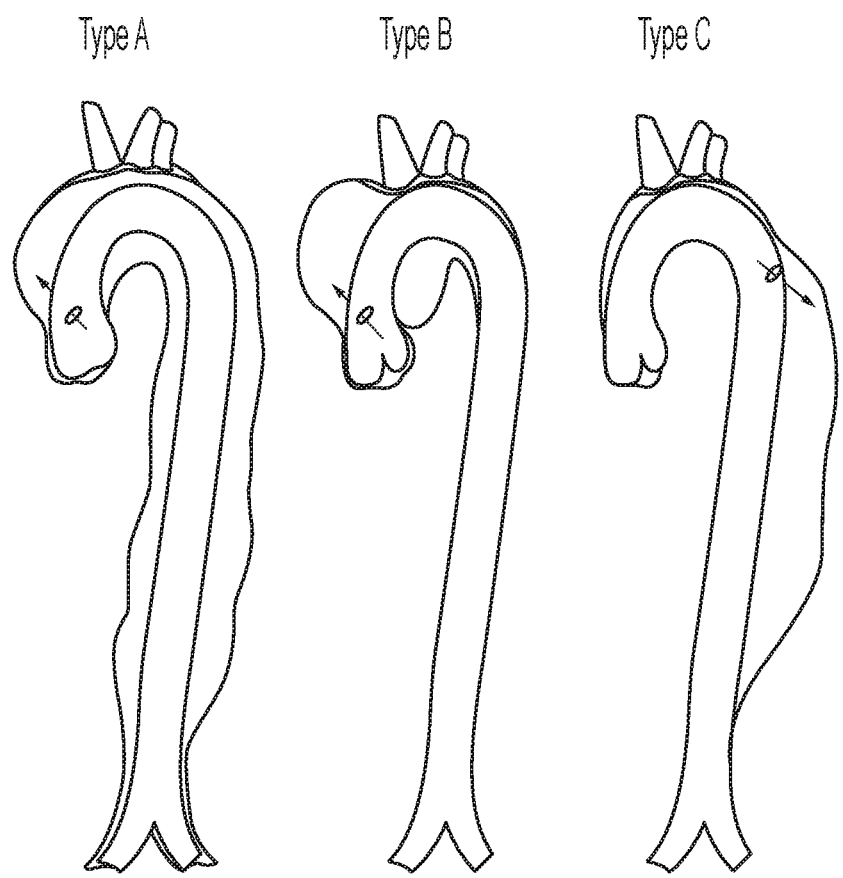
FIG. 2 depicts illustrations of various types of aortic dissections.

FIG. 2 illustrates various locations of an intimal tear. The location of the intimal tear may determine the classification of the aortic dissection. For example, an intimal tear in the ascending aorta may cause a Type A dissection. A Type B aortic dissection may include a tear that extends down the entire aorta. In either case, fixing the intimal tear with an endovascular stent graft may allow the intimal tear area to be reinforced and the false lumen to clot. A third type of tear is in the descending aorta (Type C). A Type C aortic dissection can be treated with commercially available stent grafts.

Figure 3:
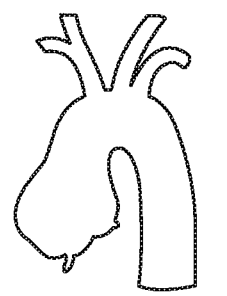
FIG. 3 depicts illustrations of various types of aortic aneurysms or an aortic dissections.
Figure 3:
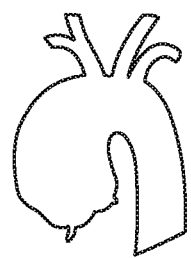
Figure 3:
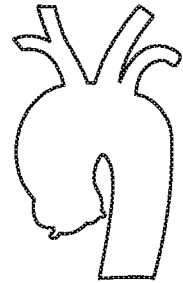
Figure 3:

FIG. 3 depicts aortic dissections that may result from aortic aneurysms. As illustrated in FIG. 3, some aneurysms do not provide a normal proximal or distal vessel. In other cases, an aneurysm may not provide a proximal or distal landing zone. For example, even where a proximal vessel is present, the proximity of the aortic valve and the coronary ostia may prevent this portion of the vessel from being utilized as a landing zone. For such aneurysms, currently available endovascular stent grafts cannot be used to repair the aortic dissection.

Various embodiments are directed towards a stent for endovascular repair comprising a stent graft having an inner surface and an outer surface, the stent graft comprising a proximal portion, a distal portion, and a plurality of fenestrations. In some embodiments, the stent may further comprise a stent fabric in mechanical communication with the outer surface of the stent graft where the stent fabric may be configured to cover at least a portion of the proximal portion of the stent graft. In further embodiments, the stent may comprise a wire constraint in mechanical communication with the inner surface of the stent graft.

In some embodiments, the wire constraint is configured to reduce a diameter of the stent graft. In some embodiments, the wire constraint may reduce the diameter of the stent graft by about 100%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or any range in between any of these values.

In some embodiments, a portion of the outer surface of the stent graft is not covered by the stent fabric.

In some embodiments, the stent may further comprise an inner stent that can be in mechanical communication with the inner or outer surface of the stent graft. In some embodiments, the inner stent is in mechanical communication with the inner surface of the stent graft. In some embodiments, the inner stent is in mechanical communication with the outer surface of the stent graft. In further embodiments, the inner stent is aligned with the plurality of fenestrations.

In some embodiments, the stent graft can be made from nitinol, stainless steel, a shape memory material, a heat-activated material, or a combination thereof. In some embodiments, the stent graft can be self-expandable, balloon expandable, or expandable by any other mechanical or other means such as, without limitation, heat.

In some embodiments, the stent fabric can be made from polytetrafluoroethylene, expandable polytetrafluoroethylene, polyester, polyethylene terephthalate, polydimethylsiloxane, polyurethane, or a combination thereof.

Figure 4:
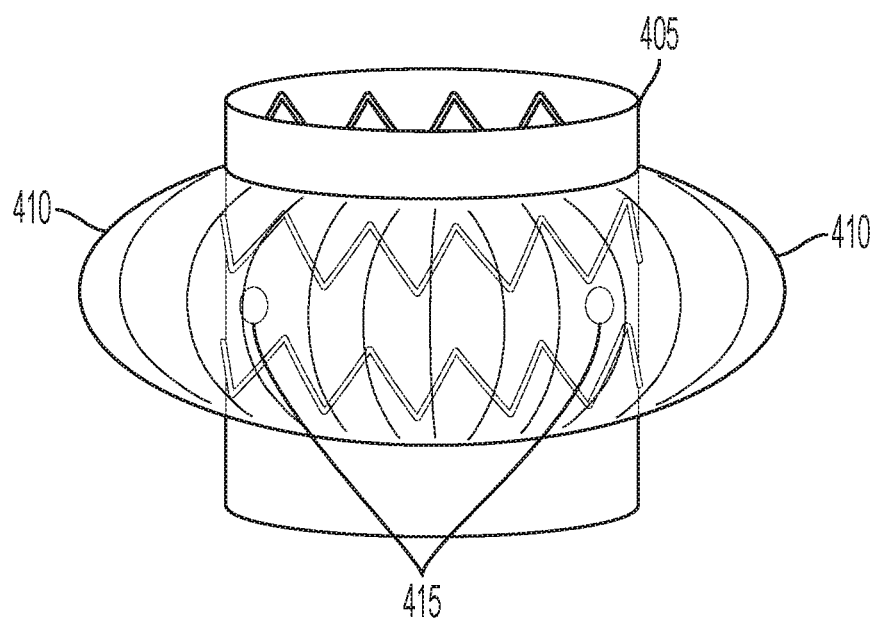
FIG. 4 illustrates a stent in accordance with an embodiment.

FIG. 4 illustrates an embodiment of a stent graft in accordance with an embodiment. In some embodiments, a stent graft 405 may include a plurality of fenestrations 415. In some embodiments, a stent fabric 410 is in mechanical communication with an outer surface of the stent graft. In some embodiments, the plurality of fenestrations 415 may allow circulating blood from the lumen of the stent graft 405 to balloon the stent fabric 410 outwardly. In some embodiments, the stent fabric 410 conforms to the anatomy or configuration of the ascending aortic aneurysm.

Figure 5:
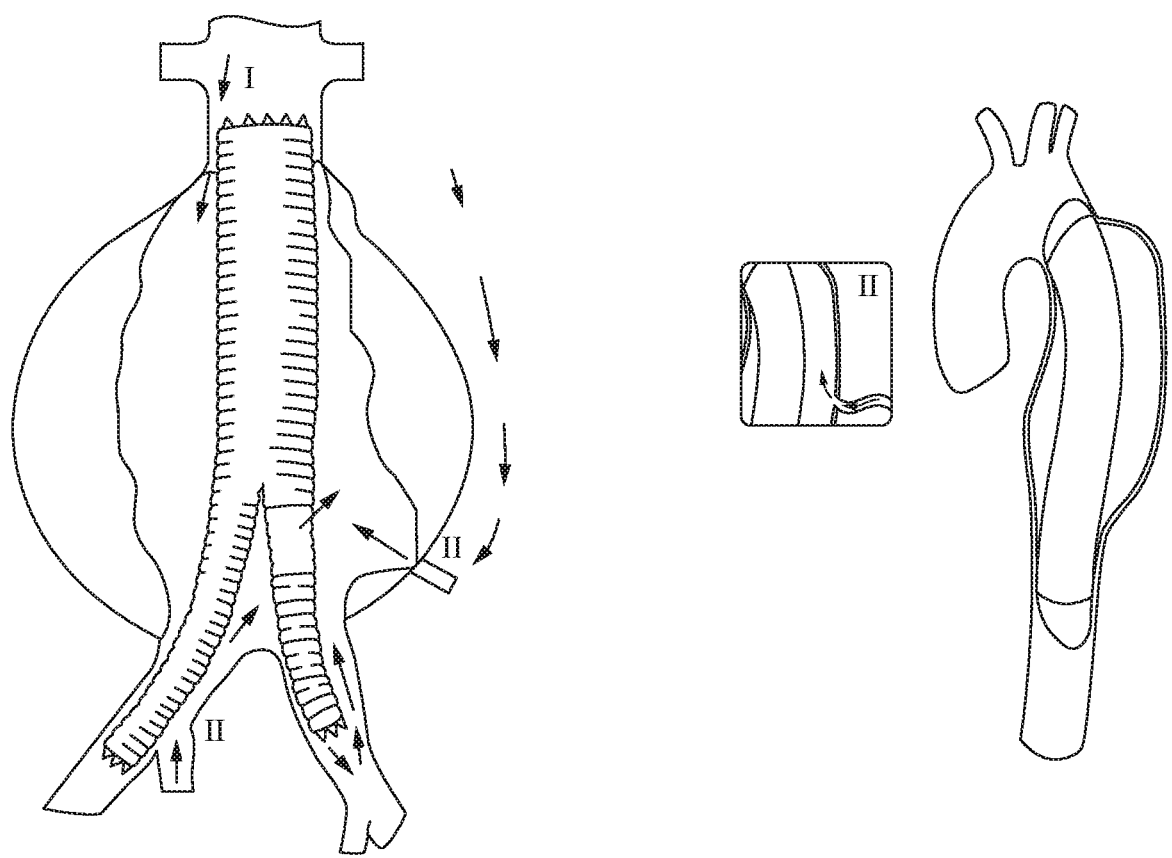
FIG. 5 depicts endoleaks in the abdominal aorta and the thoracic aorta in accordance with an embodiment.

FIG. 5 depicts type II endoleaks that may occur in the abdominal aorta or the descending thoracic aorta. Type II endoleaks can be small blood vessels arising from the aneurysm that may remain open and allow blood to re-enter the aneurysm. As such, sealing the aneurysm at the aorta may not entirely cut off blood flow to the aneurysm. In some cases, increased pressure within side branches of the aorta may result in blood being forced back into the aneurysmal sac (i.e., retrograde flow). In many cases, an aneurysm and/or dissection in the aorta may be stable despite one or more Type II endoleaks. In some cases, the Type II endoleaks may resolve spontaneously over time. However, in other cases, Type II endoleaks may prevent further complications and require additional procedures to entirely seal the aneurysm from the blood flow.

Figure 6:
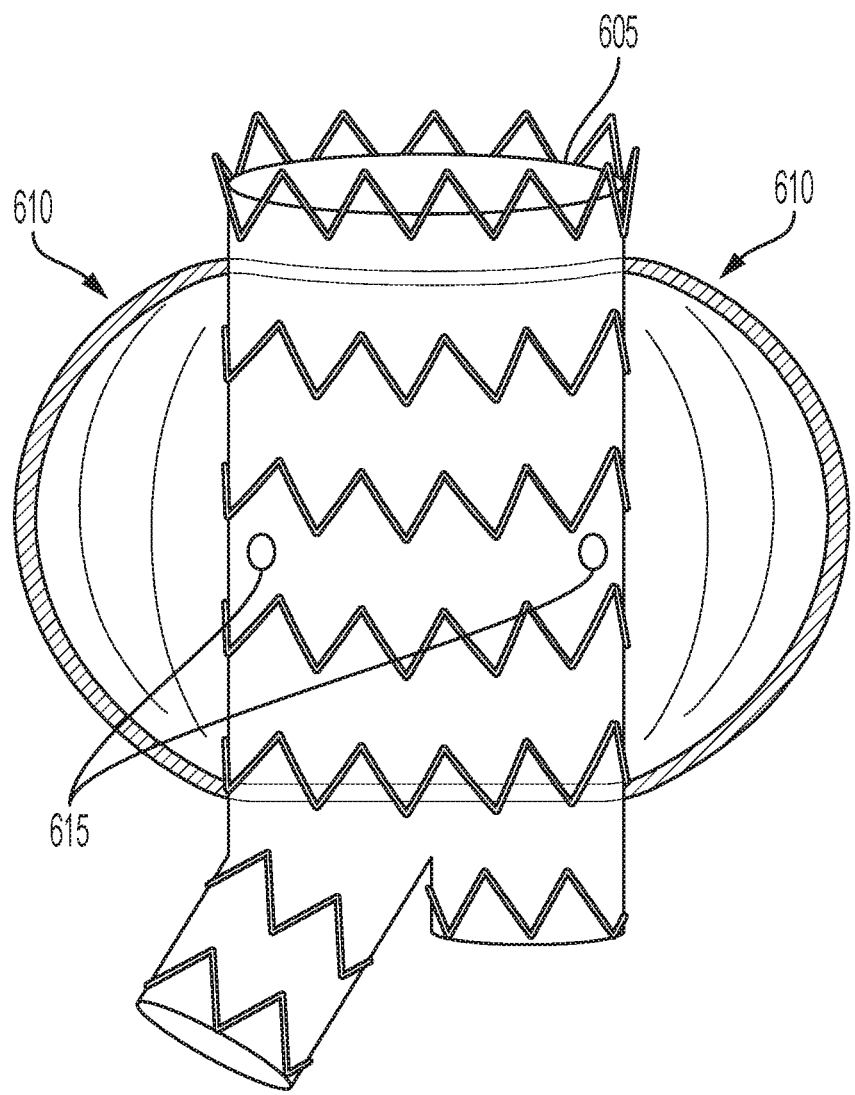
FIG. 6 illustrates a stent in the abdominal aorta in accordance with an embodiment.

FIG. 6 illustrates an embodiment of a stent graft in an infrarenal abdominal aorta. In some embodiments, a stent graft 605 has a plurality of fenestrations 615. In some embodiments, a stent fabric 610 is in mechanical communication with an outer surface of the stent graft. In some embodiments, the plurality of fenestrations 615 may allow circulating blood from the lumen of the stent graft 605 to balloon the stent fabric 610 outwardly. In some embodiments, the stent fabric 610 conforms to the anatomy or configuration of the aortic aneurysm wall, which may occlude the small blood vessels from the aneurysm and eliminate type II endoleaks.

Figure 7:
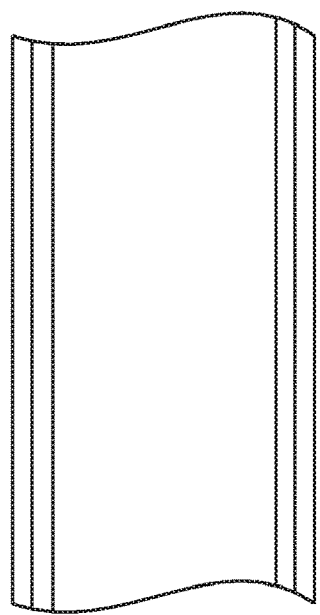
FIG. 7 depicts anatomical features of a healthy aorta and an intimal tear of the aorta in accordance with an embodiment.
Figure 7:
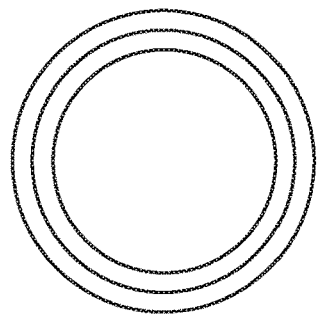
Figure 7:
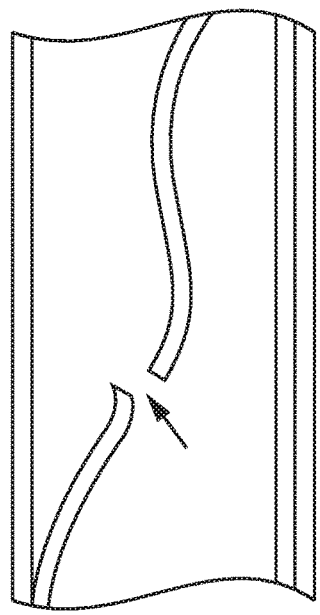
Figure 8:
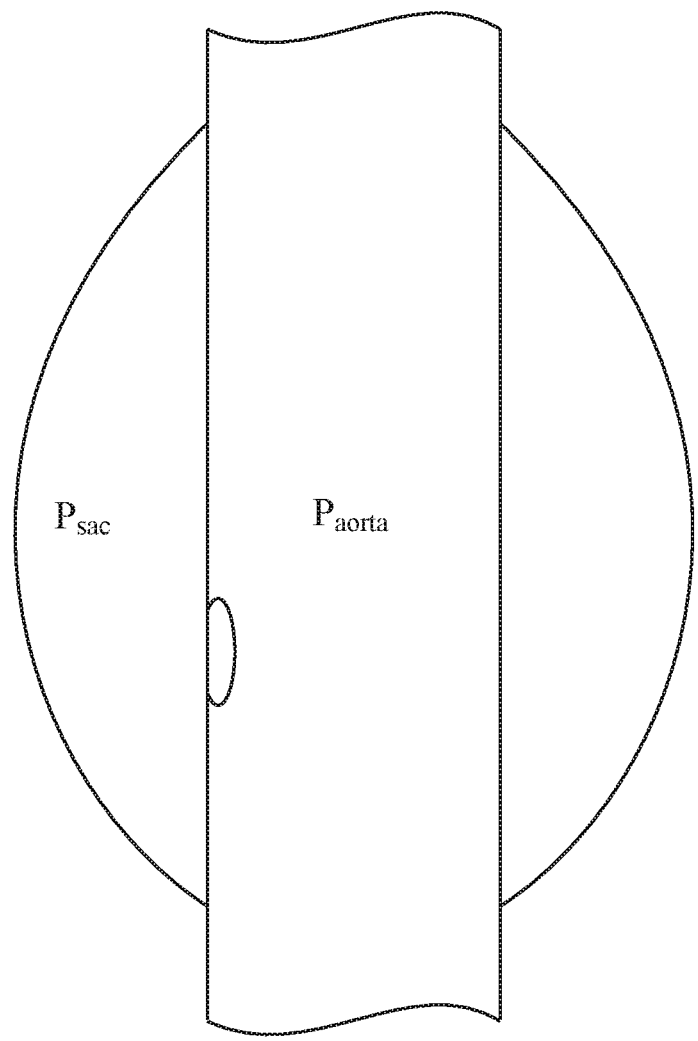
FIG. 8 depicts an aortic aneurysm, a representation of the pressure in the aorta lumen, and a representation of the pressure in the aneurysmal sac in accordance with an embodiment.

FIG. 7 illustrates a healthy or normal aorta having a single flow or true lumen. In some embodiments, aortic dissection may result from a tear or break of the intimal layer of a blood vessel. In further embodiments, an intimal tear may result in a plurality of flow lumens, including, but not limited to, the true lumen and a false lumen. In some embodiments, the false lumen has a larger diameter than the true lumen. As depicted in FIG. 8, in further embodiments, the false lumen may have a higher pressure than the true lumen.

Figure 9:
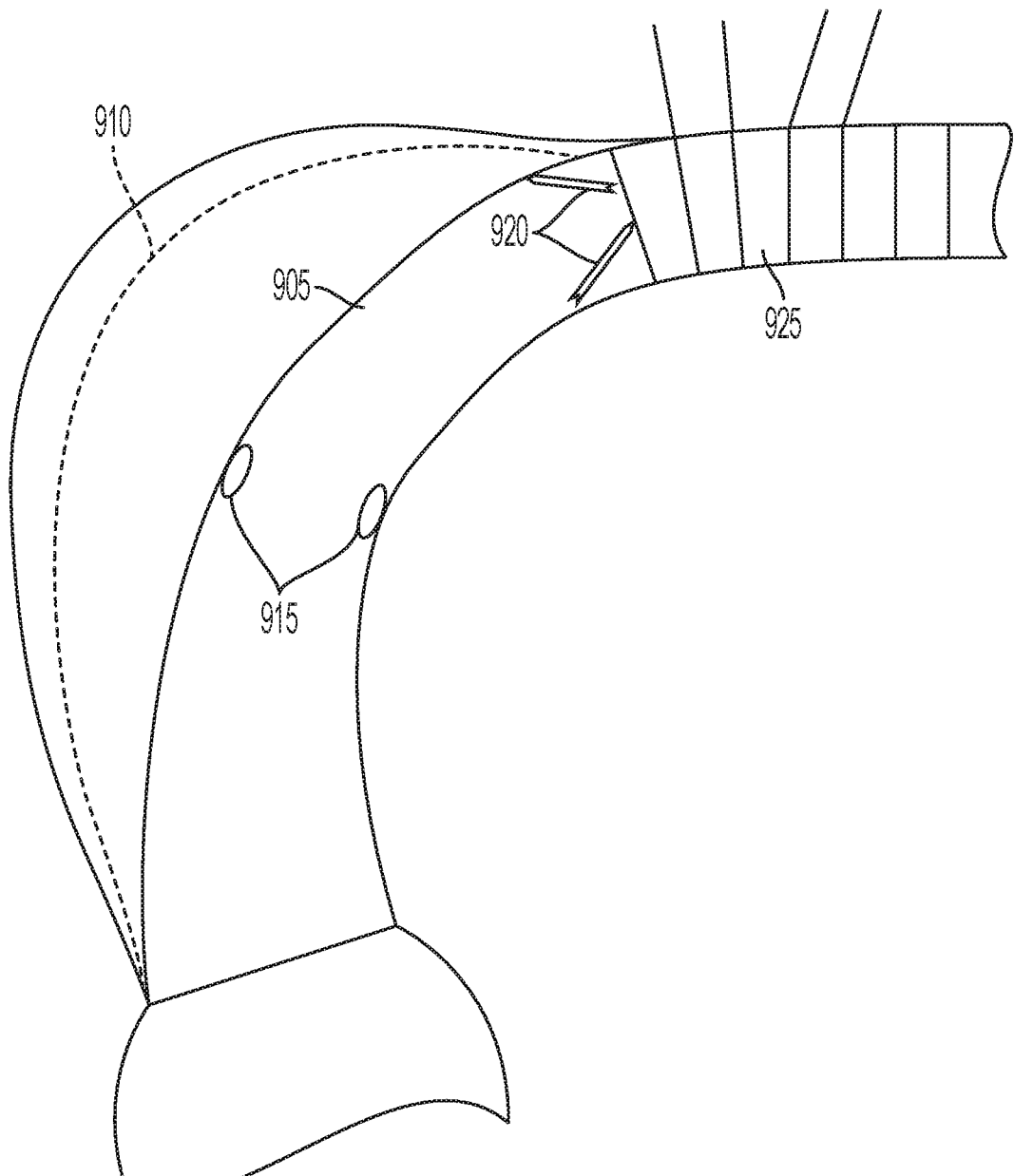
FIG. 9 depicts a stent in accordance with a further embodiment.

As illustrated in FIG. 9, various embodiments are directed towards a stent for endovascular repair comprising a stent graft 905 having an inner surface and an outer surface. The stent graft 905 comprises a proximal portion, a distal portion, and a plurality of fenestrations 915. In some embodiments, the stent may further comprise a stent fabric 910 in mechanical communication with the outer surface of the stent graft 905. The stent fabric 910 may be configured to cover at least a portion of the proximal portion of the stent graft 905. In further embodiments, the stent may comprise a wire constraint 920 in mechanical communication with the inner surface of the stent graft 905. In some embodiments, a portion 925 of the outer surface of the stent graft 905 is not covered by the stent fabric 910. In further embodiments, the portion 925 of the outer surface of the stent graft 905 that is not covered by the stent fabric is configured to prevent migration of the stent graft.

In some embodiments, the wire constraint 920 is configured to reduce a diameter of the stent graft 905. In some embodiments, the wire constraint 920 may reduce the diameter of the stent graft 905 by about 100%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or any range in between any two of these values.

In some embodiments, the stent graft 905 may be configured to conform to the radius of an aortic arch of the ascending aorta.

In some embodiments, the stent may further comprise an inner stent that can be in mechanical communication with the inner or outer surface of the stent graft 905. In some embodiments, the inner stent is in mechanical communication with the inner surface of the stent graft 905. In some embodiments, the inner stent is in mechanical communication with the outer surface of the stent graft 905. In further embodiments, the inner stent is aligned with the plurality of fenestrations 915.

In some embodiments, the plurality of fenestrations 915 of the stent graft 905 can provide fluid communication between the inner lumen of the stent graft 905 and the space between the stent graft 905 and the stent fabric 910. In some embodiments, the plurality of fenestrations 915 can be large enough to allow blood cells to enter the space. In some embodiments, the size of the plurality of fenestrations 915 can be between about 20 µm and about 5 mm. In further embodiments, the plurality of fenestrations can be in the form of holes punched into the graft material or in the form of a porous graft material. In further embodiments, the plurality of fenestrations 915 may have openings formed along at least a portion of the stent graft 905.

Figure 10A:
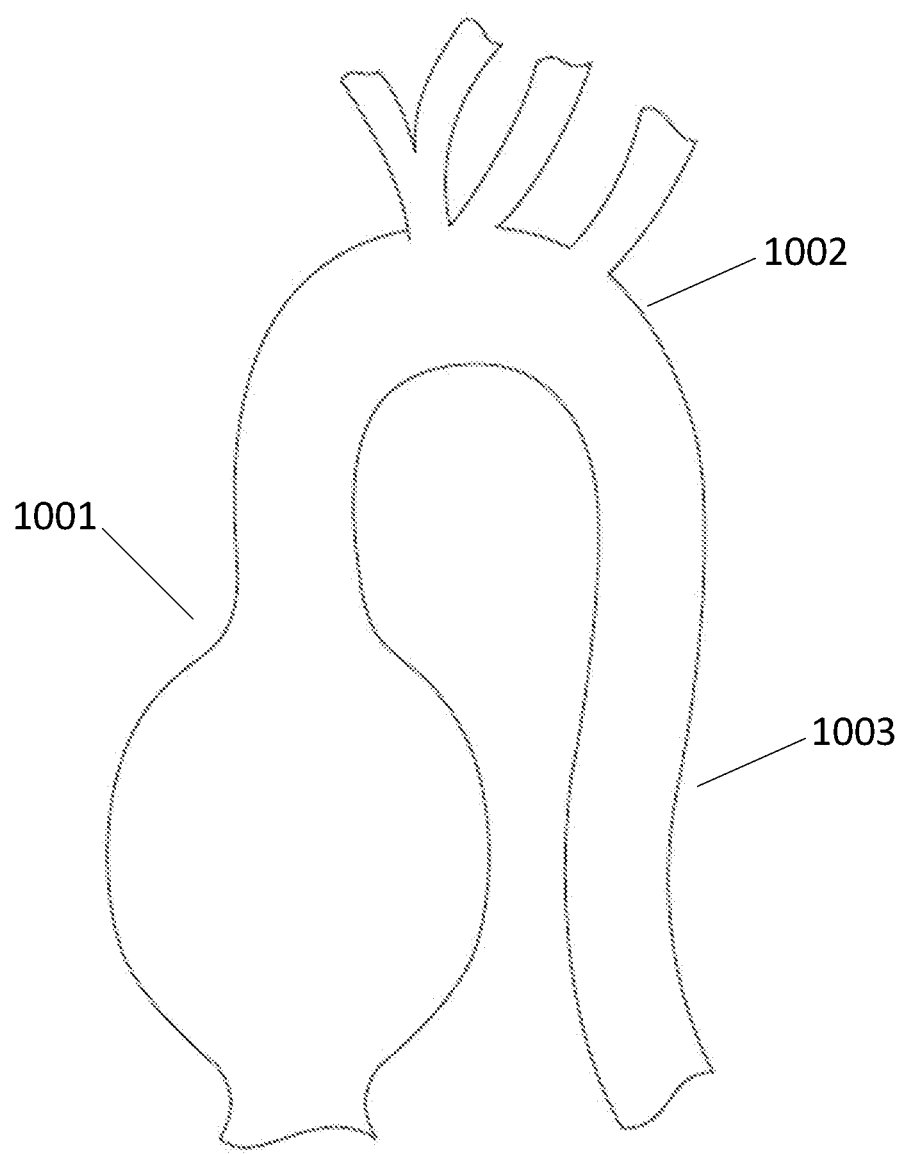
FIG. 10A depicts the anatomy of an aorta including a thoracic aortic aneurysm.

FIG. 10A depicts the anatomy of an aorta including a thoracic aortic aneurysm. As shown in FIG. 10A, the aorta may be subdivided into an ascending aorta 1001, an aortic arch 1002, and a descending aorta 1003. The ascending aorta 1001 includes the aortic root (i.e., a portion of the aorta closest to and attached to the heart and including the coronary ostia) and is situated adjacent the aortic valve and the coronary arteries of the patient's anatomy. As depicted, in the case of a thoracic aortic aneurysm, a portion of the ascending aorta 1001 may have an enlarged diameter and may further include a dissection in the wall of the aorta. The aortic arch 1002 is situated between the ascending aorta 1001 and the descending aorta 1003, and includes the great vessels (i.e., a collection of vessels including the carotid arteries, subclavian arteries, and brachiocephalic artery). The descending aorta 1003 extends through the chest, into the abdomen, and eventually splits into the common iliac arteries.

Referring now to FIGS. 10B-10C, an illustrative endovascular stent 1000 implanted in an aorta is depicted in accordance with an embodiment. As shown in FIG. 10B, the endovascular stent 1000 may be implanted in a curved or tortuous portion of a blood vessel (e.g., the ascending aorta 1001) in order to treat an aneurysm and/or dissection therein. As shown in FIG. 10C, the endovascular stent 1000 may also be implanted in a substantially straight portion of a blood vessel (e.g., the descending aorta) in order to treat an aneurysm and/or dissection therein. The endovascular stent 1000 may include an inner stent 1005 and an outer shell 1010. The inner stent 1005 forms a lumen and may include one or more openings 1015. The openings 1015 (alternatively referred to herein as fenestrations, apertures, slits, and the like) may extend radially outward from a longitudinal axis of the inner stent 1005 and/or substantially transverse to a typical direction of blood flow. In some embodiments, at least a portion of the inner stent 1005 is covered with a liquid-tight lining such that blood may not flow through the radial walls of the inner stent 1005 except through the openings 1015. The outer shell 1010 is formed from an expandable material (e.g., a fabric) and includes a first end and a second end that form a liquid-tight seal with the inner stent 1005. In some embodiments, the one or more openings 1015 are situated between the first end and the second end of the outer shell 1010. In some embodiments, the first end of the outer shell 1010 is sealed at or near a proximal end of the inner stent 1005 and the second end of the outer shell 1010 is sealed to a central portion of the inner stent 1005. However, the first end and the second end may be sealed to various locations along the inner stent 1005. In some embodiments, the entire length of the inner stent 1005 between the first end and the second end is covered by the liquid-tight lining.

FIG. 10D depicts a cross-sectional view of the endovascular stent 1000 within a blood vessel of a patient in accordance with an embodiment. As most clearly depicted therein, a liquid-tight chamber may be formed in the space between the inner stent 1005 and the outer shell 1010, and the one or more openings 1015 allow fluid communication between the lumen of the inner stent 1005 and the liquid-tight chamber.

Referring again to FIGS. 10B-10C, in some embodiments, the one or more openings 1015 are each formed with a one-way valve, thereby allowing fluid flow from the lumen of the inner stent 1005 into the liquid-tight chamber and substantially preventing fluid flow from the liquid-tight chamber into the lumen of the inner stent 1005. In additional embodiments, the openings 1015 may be formed in any of a variety of manners and with any of a variety of components to enact substantially one-way fluid flow into the liquid-tight chamber, as would be known to one having an ordinary level of skill in the art.

In some embodiments, the endovascular stent further comprises a constraint to reduce a diameter of the lumen of the inner stent 1005. For example, in some embodiments, the constraint may be a wire constraint (see for example wire constraint 920 shown in FIG. 9) that is coupled to a surface of the inner stent 1005 to pull and/or pinch a portion of the inner stent 1005 inward in order to reduce the diameter of the lumen in at least one location. In some embodiments, the reduced diameter is referred to as a constricted configuration. The constricted configuration may limit a rate of blood flow through the inner stent 1005, thereby increasing pressure within the lumen. Where the pressure within the lumen is greater than the pressure within the liquid-tight chamber, the one-way valves of the openings 1015 may open in order to fill the liquid-tight chamber and expand the outer shell 1010. In some embodiments, the wire constraint is releasable and may be removed once the outer shell 1010 has expanded to an acceptable degree, thereby reducing pressure in the lumen of the inner stent 1005. Upon removal of the constraint, the pressure in the lumen of the inner stent 1005 may be lower than the pressure within the liquid-tight chamber. As such, the one-way valves at each of the openings 1015 may close and do not need to be permanently closed or blocked in any other manner. While the constraint may be formed as a releasable wire, the constraint may also be formed as one or more internal flaps or obstructions within the lumen. However, the constraint may be formed as any moveable or releasable structure which narrows the diameter of the lumen or otherwise impedes flow to increase pressure within the lumen as would be known to one having an ordinary level of skill in the art.

In some embodiments, the endovascular stent 1000 further comprises an anchor 1025 extending beyond the outer shell 1010. In some embodiments, the anchor 1025 may extend distally of a distal end (i.e., a distal-most end of the first and second ends) of the outer shell 1010 (as depicted in FIG. 10B). In some embodiments, the anchor 1025 may extend proximally of a proximal end (i.e., a proximal-most end of the first and second ends) of the outer shell 1010 (as depicted in FIG. 10C). As shown in FIGS. 10B-10C, the anchor 1025 may be formed as a portion of the inner stent 1005 extending beyond the outer shell 1010. In some embodiments, the anchor portion 1025 of the inner stent 1005 may be an uncovered or open portion, such as a bare metal stent. In all of its various contemplated forms, the anchor 1025 serves to provide stability and maintain an implanted position of the endovascular stent 1000, particularly when the outer shell 1010 is not fully expanded.

Figure 11:
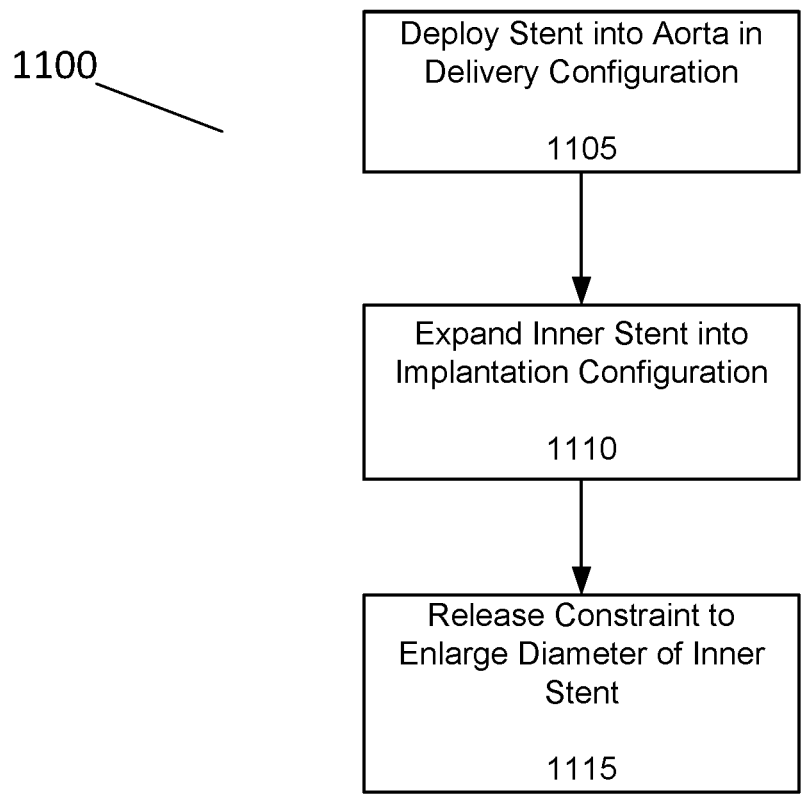
FIG. 11 depicts a flow diagram of an illustrative method of stabilizing an aortic aneurysm and/or aortic dissection in accordance with an embodiment.

FIG. 11 depicts a flow diagram 1100 of an illustrative method of stabilizing an aortic aneurysm and/or aortic dissection in accordance with an embodiment. As shown in FIG. 11, a stent according to any of the embodiments described herein (e.g., endovascular stent 1000) may be deployed 1105 into an aorta in a delivery configuration. In some embodiments, the inner stent and outer shell may be compressed in the delivery configuration such that the stent is easily navigated through the patient's anatomy. In some embodiments, deploying the catheter comprises utilizing a delivery catheter or other delivery device as is typically utilizing for stent delivery and implantation and would be known to one having an ordinary level of skill in the art. For example, a delivery catheter may be inserted into a blood vessel of the patient and one or more guide wires may be extended therefrom and positioned adjacent the aneurysm and/or dissection. In some embodiments, the stent may be advanced over the one or more guide wires in the delivery configuration and positioned with respect to the aneurysm and/or dissection. The inner stent may be expanded 1110 from the compressed configuration to an implantation configuration. For example, the inner stent may comprise a self-expanding material, a shape memory material (e.g., nitinol) or other material requiring activation, and/or may be mechanically expanded such as by inflation of a balloon component of the delivery system. In some embodiments, the diameter of one or more portions of the stent in the implantation configuration may be substantially similar to a native healthy diameter of the vessel. In both the compressed configuration and the implantation configuration, however, the stent may maintain the constriction configuration as described herein, thereby maintaining at least a portion of the stent at a reduced diameter with respect to the remainder of the stent. Due to the constricted configuration, blood flow through the stent will naturally elevate pressure within the lumen of the inner stent, thereby directing blood flow through the one or more openings and expanding the outer shell. As the outer shell expands, the outer shell may contact one or more portions of the aneurysm and seal the aneurysm from the healthy vessel portions located proximally and distally thereof (e.g., as shown in FIGS. 10B-10C), thereby preventing blood flow into the aneurysm and/or a false lumen caused by an aortic dissection. In the case of an aortic dissection, the outer shell may further compress against and/or seal a tear in the wall of the aorta (e.g., an intimal tear). In some embodiments, the outer shell may compress the aortic dissection and reduce the size of a false lumen. When the outer shell has sufficiently expanded to seal the aneurysm, the constraint may be released 1115 to move the stent from the constricted configuration to an expanded configuration where the portion of the stent having a reduced diameter is expanded to an enlarged diameter. For example, the diameter may be enlarged to substantially match the remainder of the stent and/or a native healthy diameter of the vessel.

In some embodiments, the liquid-tight chamber has a greater pressure than the lumen of the inner stent. As such, the one-way valves of the one or more openings may close. Over time, the blood within the liquid-tight chamber may clot and stabilize. In many cases, the clot cannot escape back into the blood flow and thus does not pose a significant risk.

In some embodiments, expansion of the outer shell seals blood flow to and from the aneurysm. As such, the blood remaining therein may clot and stabilize, thereby reducing the risk of a rupture. In some embodiments, the false lumen of the dissection may connect to additional flow paths. For example, Type II endoleaks (as depicted and described with respect to FIG. 5) may cause additional flow paths from the false lumen. In some cases, additional downstream tears in the aortic wall may provide flow paths (i.e., flow back into the true lumen downstream of the site being treated). As such, expansion of the outer shell and compression of the false lumen may force the flow through the additional flow paths and out of the false lumen.

As the major inflow to the aneurysm is sealed by the stent, the aneurysm may be stable. In some cases, additional procedures and/or additional stents may be utilized to repair the additional tears. For example, it is common for patients with one aortic dissection to be vulnerable or susceptible to additional tears in the aorta and may require additional treatments during their lifespan. As such, it is contemplated that an additional stent as described herein may be utilized for each tear along the aorta. However, the embodiments described herein are additionally compatible with a variety of commercially available and approved stent devices. For example, while one tear (such as an ascending aortic dissection) may be treated with a stent described herein, any variety of commercially available and approved stents may be utilized to treat additional tears (such as descending aortic dissections which do not present a tortuous environment as in the ascending aorta) without any interference or risk to the ascending aortic dissection. As may be necessary in some cases, the uncovered bare metal anchor portion of the inner stent may provide an interface portion for additional stents or any variety of additional devices that may be used for assessment or treatment of the vasculature.

While the apparatuses and methods herein are described with respect to use in an ascending aorta and/or descending aorta, it is contemplated that the apparatuses and methods may be utilized in a wide variety of scenarios. For example, the described apparatuses and methods may be utilized to treat aneurysms and/or dissections in any portion of the aorta as well as additional arteries, veins, and blood vessels as would be known to one having an ordinary level of skill in the art. In all cases, the ability of the embodiments described herein to adapt to a tortuous and/or irregular anatomy provides a significant advantage over currently available stents.

This disclosure is not limited to the particular apparatus, systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In the detailed description above, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different devices or applications. Various presently unforeseen or unanticipated alternatives, modifications, variations or improvements therein may be subsequently made by those skilled in the art, each of which is also intended to be encompassed by the disclosed embodiments.

What is claimed is:

1. A stent for endovascular repair, comprising:
   an inner stent comprising a circumferential wall defining a central lumen and one or more fenestrations extending through the circumferential wall, each fenestration configured to permit passage of blood therethrough, wherein at least a portion of the central lumen is configurable between a constricted diameter state and an expanded diameter state; and
   an expandable outer shell having a first end and a second end and forming a liquid-tight seal with the circumferential wall of the inner stent at each of the first end and the second end to define an outer chamber, wherein the expandable outer shell is configured to expand from a collapsed configuration to a deployed configuration responsive to the passage of blood through the one or more fenestrations into the outer chamber, wherein at least a portion of the expandable outer shell is configured to conform to at least a portion of a blood vessel in the deployed configuration to anchor the stent within the blood vessel, wherein in the constricted diameter state, a pressure in the central lumen is greater than a pressure in the outer chamber.

2. The stent of claim 1, wherein the inner stent comprises a liquid-tight lining between the first end and the second end of the expandable outer shell such that the outer chamber is a liquid-tight chamber.

3. The stent of claim 2, wherein each of the one or more fenestrations comprises a one-way valve configured to permit passage of blood from the central lumen to the liquid-tight chamber.

4. The stent of claim 1, further comprising a releasable wire constraint configured to maintain the at least a portion of the central lumen in the constricted diameter state.

5. The stent of claim 1, further comprising a distal anchor extending beyond the expandable outer shell and configured to fix a position of the stent within the blood vessel.

6. The stent of claim 5, wherein the distal anchor is located distally of the second end of the expandable outer shell.

7. The stent of claim 1, wherein the inner stent is formed from a material selected from the group consisting of nitinol, stainless steel, a shape memory material, a heat activated material, and a combination thereof.

8. The stent of claim 1, wherein the expandable outer shell is formed from a material selected from the group consisting of polytetrafluoroethylene, polyester, polyethylene terephthalate, polydimethylsiloxane, polyurethane, and a combination thereof.

9. A method of stabilizing an aortic dissection defining an intimal tear in an ascending aorta of a patient, the method comprising:
providing an endovascular stent including:
an inner stent comprising a circumferential wall defining a central lumen and one or more fenestrations extending through the circumferential wall, each fenestration configured to permit passage of blood therethrough, wherein at least a portion of the central lumen is capable of shifting between a constricted diameter state and an expanded diameter state; and
an expandable outer shell having a first end and a second end and forming a liquid-tight seal with the circumferential wall of the inner stent at each of the first end and the second end to define an outer chamber; and
deploying the endovascular stent into the ascending aorta with the expandable outer shell in a collapsed configuration, whereby the expandable outer shell expands from the collapsed configuration to a deployed configuration responsive to the passage of blood through the one or more fenestrations and into the outer chamber, wherein at least a portion of the expandable outer shell conforms to a shape of at least a portion of the ascending aorta in the deployed configuration, wherein in the constricted diameter state, a pressure in the central lumen is greater than a pressure in the outer chamber, thereby directing blood through the one or more fenestrations and into the outer chamber.

10. The method of claim 9, wherein the expandable outer shell is further capable of sealing the intimal tear in the deployed configuration.

11. The method of claim 9, wherein the expandable outer shell is further capable of compressing the aortic dissection in the deployed configuration.

12. The method of claim 9, wherein the endovascular stent further comprises a releasable wire constraint capable of maintaining the at least a portion of the central lumen in the constricted diameter state.

13. The method of claim 12, further comprising releasing the wire constraint to shift the at least a portion of the central lumen from the constricted diameter state to the expanded diameter state.

14. The method of claim 13, wherein in the expanded diameter state, the pressure in the central lumen is less than or equal to the pressure in the outer chamber, thereby directing blood through the central lumen.

15. The method of claim 9, wherein the inner stent comprises a liquid-tight lining between the first end and the second end of the expandable outer shell such that the outer chamber is a liquid-tight chamber.

16. The method of claim 15, wherein each of the one or more radial fenestrations comprises a one-way valve configured to permit passage of blood from the central lumen to the liquid-tight chamber.

17. The method of claim 9, wherein the endovascular stent further comprises a distal anchor extending beyond the expandable outer shell, wherein the method further comprises anchoring the endovascular stent with the distal anchor to fix a position of the endovascular stent within the ascending aorta.

18. The method of claim 17, wherein the distal anchor is located distally of the second end of the expandable outer shell.

* * * * *